United States Patent
Zhu et al.

(10) Patent No.: US 7,230,016 B2
(45) Date of Patent: Jun. 12, 2007

(54) PIOGLITAZONE SALTS, SUCH AS PIOGLITAZONE SULFATE, AND PHARMACEUTICAL COMPOSITIONS AND PROCESSES USING THE SAME

(75) Inventors: Jie Zhu, Nijmegen (NL); Frantisek Picha, Brno (CZ)

(73) Assignee: Synthon IP Inc., Gainesville, VA (US)

( * ) Notice: Subject to any disclaimer, the term of this patent is extended or adjusted under 35 U.S.C. 154(b) by 0 days.

(21) Appl. No.: 10/842,696

(22) Filed: May 11, 2004

(65) Prior Publication Data

US 2005/0054684 A1    Mar. 10, 2005

Related U.S. Application Data

(60) Provisional application No. 60/469,838, filed on May 13, 2003.

(51) Int. Cl.
*A61K 31/4439* (2006.01)
*C07D 417/12* (2006.01)

(52) U.S. Cl. .................... 514/342; 546/269.7

(58) Field of Classification Search ............. 546/269.7; 514/342
See application file for complete search history.

(56) References Cited

U.S. PATENT DOCUMENTS

| 4,287,200 | A | 9/1981 | Kawamatsu et al. |
| 4,438,141 | A | 3/1984 | Kawamatsu et al. |
| 4,582,839 | A | 4/1986 | Meguro et al. |
| 4,687,777 | A | 8/1987 | Meguro et al. |
| 5,965,584 | A | 10/1999 | Ikeda et al. |
| 5,965,589 | A | 10/1999 | Sohda et al. |
| 5,990,139 | A | 11/1999 | Yano et al. |
| 6,207,690 | B1 | 3/2001 | Urban et al. |
| 6,271,243 | B1 | 8/2001 | Ikeda et al. |
| 6,288,096 | B1 | 9/2001 | Andersson et al. |
| 2005/0059708 | A1 | 3/2005 | Pospisilik et al. |

FOREIGN PATENT DOCUMENTS

| EP | 0 008 203 A1 | 2/1980 |
| EP | 0 283 035 A1 | 9/1988 |
| EP | 0 193 256 B1 | 4/1989 |
| EP | 0 506 273 B1 | 5/1995 |
| WO | WO 02/088120 A1 | 11/2002 |

OTHER PUBLICATIONS

Arakawa et al., "Novel Benzoxazole 2,4-Thiazolidinediones as Potent Hypoglycemic Agents. Synthesis and Structure-Activity Relationships," Chem. Pharm. Bull. 45(12) pp. 1984-1993 (1997).
Kitajima et al. I "Preparation of 3-Aromatic, etc.,", CA 134:41915 (2000).
Takeno et al., "Preparation of (oxazolyl), etc., " CA 126:89361 (1997).
Kitajima et al. II, "Hybridization of Non-Sulfonylurea, etc., "Bioorganic & Medicinal Chemistry Letters, 10(2000) 2453-2456.

*Primary Examiner*—Patricia L. Morris
(74) *Attorney, Agent, or Firm*—Mark R. Buscher

(57) ABSTRACT

Water-soluble salts of pioglitazone especially pioglitazone sulfate are useful in pharmaceutical applications.

20 Claims, No Drawings

PIOGLITAZONE SALTS, SUCH AS PIOGLITAZONE SULFATE, AND PHARMACEUTICAL COMPOSITIONS AND PROCESSES USING THE SAME

This application claims the benefit of priority under 35 U.S.C. § 119(e) from U.S. Provisional Application Ser. No. 60/469,838, filed May 13, 2003, the entire contents of which are incorporated herein by reference.

BACKGROUND OF THE INVENTION

The present invention relates to salts of pioglitazone including water-soluble salts of pioglitazone, pharmaceutical compositions comprising these salts, and processes of using these salts.

Pioglitazone, chemically 5-[[4-[2-(5-ethyl-2-pyridinyl)-ethoxy]phenyl]methyl]-2,4-thiazolidinedione, of the formula (1):

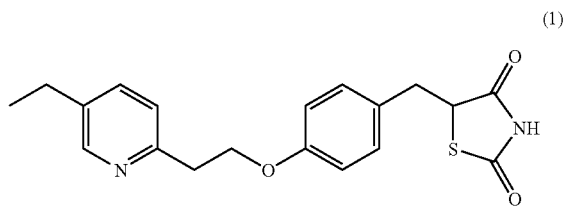

(1)

is an antidiabetic agent. Pharmaceutical compositions comprising pioglitazone, as the hydrochloride salt, are marketed under the brand name ACTOS® (Takeda Chemical Ind.) for treatment of type II diabetes. Pioglitazone hydrochloride is generally considered to be an odorless white crystalline powder with a melting point of 193–194° C. It is known to be slightly soluble in anhydrous ethanol, very slightly soluble in acetone and acetonitrile, practically insoluble in water, and insoluble in ether. However, pioglitazone hydrochloride dissolves well in N,N-dimethylformamide and dimethyl-sulfoxide.

EP 193256 and corresponding U.S. Pat. No. 4,687,777 disclose a class of thiazolidinedione derivatives and specifically disclose pioglitazone. These documents also disclose that the thiazolidinedione derivatives may be converted to a pharmacologically acceptable salt by using an acid or a base. The classes of acid salts include mineral salts (e.g., hydrochloride, hydrobromide, sulfate, etc.), organic acid salts (e.g., succinate, maleate, fumarate, malate, tartrate, etc.), and sulfonates (e.g., methanesulfonate, benzenesulfonate, toluenesulfonate, etc.). The base salts include alkali metal salts, e.g., sodium salt, potassium salt, and alkaline earth metal salts, e.g., calcium salt, etc. The examples in these documents include isolating pioglitazone as a base and as a sodium salt; see Examples 1(d) and 1(e), respectively, of U.S. Pat. No. 4,687,777.

Pioglitazone hydrochloride exhibits properties that make it suitable for many pharmaceutical purposes. It is an easily handled crystalline material, stable at room temperature and under moisture. However, it is extremely insoluble in water and is not suitable for making aqueous pharmaceutical solutions.

It would be desirable to have a water-soluble salt of pioglitazone for manufacturing and/or formulation purposes. For example, such a salt could be useful in making liquid pharmaceutical dosage forms, for instance oral solutions or injectable formulations.

SUMMARY OF THE INVENTION

The present invention relates to the discovery of water-soluble pioglitazone salts and the effect of water on pioglitazone salts. Specifically, a first aspect of the invention relates to a pioglitazone sulfate. The pioglitazone sulfate can be in any form including a solid form, preferably a crystalline form, as well as a dissolved form.

Another aspect of the invention relates to a pharmaceutical composition, comprising a pioglitazone sulfate and at least one pharmaceutically acceptable excipient. The pharmaceutically acceptable excipient is preferably a liquid carrier, such as water, or a solid carrier, binder, or diluent. In aqueous-based compositions, a solution stabilizer, such as a polymer, is preferably also included.

Still another aspect of the invention relates to a process of treating a hypoglycemia disorder, which comprises administering an effective amount of the pharmaceutical composition of the invention to a patient in need of such treatment.

Yet another aspect of the invention relates to a process, which comprises reacting pioglitazone or a salt thereof, other than a pioglitazone sulfate, with sulfuric acid in a solvent to form pioglitazone sulfate. Preferably the solvent is methanol.

In another aspect, the invention relates to a process, which comprises contacting a pioglitazone salt with water for a sufficient time to precipitate solid pioglitazone base therefrom. The water preferably does not contain a neutralizing agent.

DESCRIPTION OF THE INVENTION

As an overview, the present invention includes the discovery of water-soluble pioglitazone salts, especially water-soluble acid addition salts such as pioglitazone sulfate. The water-soluble salts may be included in pharmaceutical compositions that also include at least one pharmaceutically acceptable excipient. These pharmaceutical compositions may be used in processes of treating hypoglycemia disorders.

As used herein a pioglitazone salt is considered "water-soluble" if a salt concentration of at least 7 mg/ml can be achieved, even if only momentarily, in distilled water at 25° C. Preferably, the salt exhibits a water solubility of at least 10 mg/ml, more preferably at least 20 mg/ml.

Pioglitazone may form salts with acids ("acid addition salts") or with bases ("base salts"). To produce a pioglitazone acid addition salt, a strong acid is generally needed because of the weak basicity of the pioglitazone molecule. In this regard, weak acids often do not yield pioglitazone salts. For instance, after stirring a suspension of pioglitazone base in a methanol solution of a weak acid (an acid having a pKa greater than 1.5 such as maleic or phosphoric acid), the starting material is completely recovered and no salt is formed.

The aqueous solubility of several pioglitazone salts derived from strong acids or bases is listed in the table below. In the following table, "(dec.)" indicates that the salt decomposed before melting.

|  | m.p. (° C.) | soluble in H$_2$O |
|---|---|---|
| Acid Addition Salt | | |
| Hydrochloride | 191~193 | No |
| Hydrobromide | 193~196 | No |
| Sulfate | 105~115 | Yes |
| Mesylate | >70 (dec.) | Yes |
| Tosylate | 135~137 | — |
| 2-Napsylate | 110~120 | Slight |
| Edisylate | 158~165 | Yes |
| Base Salt | | |
| Na salt | 251~254 | yes* |
| K salt | 162~166 | yes* |
| Ca salt | >80 (dec.) | yes* |
| Choline salt | >80 (dec.) | yes* |

*The salt is dissolved in water to form a blurred solution.

Some of the pioglitazone salts dissolved instantly in water, such as the sulfate, mesylate, and ethane-di-sulfonate (edisylate) salts. The hydrochloride, consistent with the prior art understanding, did not dissolve in water. The base salts also dissolved in water but they typically formed an unclear solution. The water-soluble salts of pioglitazone are useful as active agents in forming a pioglitazone pharmaceutical composition, especially solid dosage forms, as is described herein after.

Surprisingly, the water solutions of the above salts (if dissolved) are not completely stable and eventually yield a suspension. Depending on the salt, the precipitation of a solid begins as quickly as within a few minutes or after several hours. The time of precipitation also depends on nucleation. In particular, once a solid forms, the solution quickly precipitates to form a complete suspension. The precipitated solid is, rather surprisingly, pioglitazone base and not the pioglitazone salt.

Interestingly, when a methanolic solution of pioglitazone HCl salt is poured into water, the pioglitazone base quickly precipitates without using any base (neutralizing agent) to neutralize the acid salt. This precipitation in water indicates that the solubility of pioglitazone base in water is so low that the equilibrium is completely shifted to the formation of pioglitazone base.

While not wishing to be bound by theory, it is believed that pioglitazone base is a neutral non-ionic species rather than a zwitter-ion. This theory is supported by a large difference in the $^1$H NMR proton shifts on the pyridine ring in the base and in the salt.

One aspect of the present invention is based on this phenomenon. Specifically, contacting a pioglitazone salt with a sufficient amount of water for a sufficient time precipitates pioglitazone base. The salt can be an acid addition salt or a base salt and can be water-soluble or water-insoluble. The contact can be carried out by combining an organic solvent solution of the pioglitazone salt with water, or, by dissolving a water-soluble salt of pioglitazone in an aqueous media. The duration of contact is not particularly limited, but for practical considerations it is usually preferred to achieve precipitation within one hour, more preferably within 30 minutes, and generally substantially upon contact, e.g. within 5 minutes. The amount of water is not particularly limited and need only be sufficient to achieve the precipitation effect. In general, the amount of water corresponds to at least 1 ml per 10 grams of salt, e.g. 1 ml per 1 g, or 1 ml per 0.1 g, but is not limited thereto. While a neutralizing agent, i.e. an acid or a base, can be present, such is not necessary and is preferably omitted. This process is particularly useful for isolating pioglitazone base from a crude reaction medium. The pioglitazone can be reacted with an acid or base to form a salt and then water can be added to induce precipitation of the pioglitazone base. Alternatively, a pioglitazone salt, especially a water-soluble salt of pioglitazone, can be formed and precipitated from the reaction media, isolated, and then dissolved in an aqueous media whereby after sufficient time a pioglitazone base is precipitated. By using two different kinds of media, one may remove both hydrophilic and lipophilic impurities from the crude pioglitazone base.

Further, regarding the water-soluble salts of pioglitazone, the ability to precipitate the pioglitazone base can be useful in designing a pharmaceutical composition for delivering pioglitazone base, bearing in mind that gastric and intestinal fluids are aqueous media.

Of the water-soluble salts, pioglitazone sulfate is the most preferred. As used herein "pioglitazone sulfate" means the salt formed from pioglitazone and sulfuric acid. The salt preferably has approximately a 1:1 molar ratio of pioglitazone moiety to sulfuric acid moiety, especially in solid form. It has superior aqueous solubility and can stably remain in an aqueous solution for hours. Pioglitazone sulfate may be isolated in solid state as a white or almost white crystalline material. It melts at a temperature of about 105 to 115° C., without decomposition. DSC analysis shows a single melting endotherm. The solid compound is not hygroscopic. Pioglitazone sulfate is thus an especially useful form of pioglitazone for making pharmaceutical formulations, e.g., as an active agent.

Although aqueous solutions of pioglitazone sulfate will eventually, after a trace of solid appears, turn into a suspension of pioglitazone base, pioglitazone sulfate solutions can be stabilized. Specifically, a solution stabilizer can be effectively added to a pioglitazone sulfate aqueous solution to enhance the stability. As used herein a "solution stabilizer" is an additive that when present in some amount in an aqueous pioglitazone sulfate solution, provides a statistically significant delay in the precipitation of pioglitazone base from the solution in comparison to the same solution held under the same conditions but without the solution stabilizer contained therein. Preferably, a stabilized solution, i.e., a pioglitazone sulfate solution that contains a solution stabilizer, does not precipitate pioglitazone base for at least one week, more preferably at least one month, still more preferably at least three months, and still more preferably at least six months, at 25° C. in a sealed container. Typically the solution stabilizer is a polymer, such as a water-soluble polymer, or a crown-ether. The solution stabilizer may be fully dissolved, partly dissolved and/or swelled, or not dissolved in the aqueous solution, but is preferably dissolved therein. Preferably the solution stabilizer is hydroxypropylmethylcellulose (HPMC), polyvinylpyrrolidone, or cyclodextrin, and most preferably HPMC. The amount of solution stabilizer is generally within the range of 1 to 500 mg/ml of the solution, typically 1 to 200 mg/ml, more typically 10 to 100 mg/ml. A stabilized pioglitazone sulfate solution is thus especially useful as a liquid pharmaceutical formulation and/or for making a liquid pharmaceutical formulation.

The pioglitazone salts of the present invention can be made by conventional salt forming reactions between pioglitazone and an appropriate acid in a solvent. Pioglitazone sulfate can be made, for example, by reacting a pioglitazone base or a salt thereof (other than the pioglitazone sulfate) with sulfuric acid in a solvent. Generally the solvent is a lower aliphatic alcohol, a lower aliphatic ketone such as acetone, or an ether such as diethylether or tetrahydrofuran. Preferably, the solvent is comprised in whole or in part of a lower aliphatic alcohol (e.g., $C_1$ to $C_4$ alcohols), such as methanol, because they dissolve pioglitazone base to a suitable extent and they are also able to dissolve a lot of the acids and bases that are used for making the salts. If the solubility of the pioglitazone base or the acid in the alcohol solvent is found to be insufficient for the intended purpose, it may be enhanced by common means, e.g., by heating the mixture (optionally up to reflux) or adding a co-solvent enhancing the solubility.

With reference to pioglitazone sulfate, a stoichiometric equivalent of the sulfuric acid relative to the pioglitazone base is generally used, but a slight excess of the sulfuric acid, e.g. up to 10% molar excess, may be used as well. Other ratios can also be used such as 2:1. The temperature of the contact may be ambient, but the reaction mixture can also be heated, optionally up to reflux of the solvent, and is generally in the range of 10 to 50° C.

The pioglitazone sulfate can precipitate from the solution spontaneously, but more likely some step such as cooling, concentrating, adding a seeding crystal, or adding a contrasolvent is advantageously and/or necessarily carried out. As pioglitazone sulfate is soluble in methanol, the addition of a contrasolvent is advantageous for precipitating the solid state salt. Useful contrasolvents, i.e., solvents in which the salt is less soluble than the solution solvent, include less polar solvents such as an ether or an aliphatic hydrocarbon such as hexane or heptane, or a combination of both. The size and shape of the formed crystals may be modified by known ways, for instance by precipitation regimen or by using crystallization modifiers.

Before precipitation, the solution of pioglitazone sulfate may be treated by a suitable adsorption material such as activated carbon or silica to remove traces of impurities, such as colored impurities, to enhance the overall purity of the product.

After precipitation, pioglitazone sulfate may be isolated from the reaction mixture by methods such as filtration or centrifugation, optionally washed with a suitable liquid (such as the contrasolvent) and dried, such as in vacuo. The isolated product may be isolated in solvated form, the solvent may, however, be removed by drying.

Solid state pioglitazone sulfate is a stable, easily handled solid material, and it may be used as an equivalent to pioglitazone hydrochloride in pharmaceutical compositions for treating pioglitazone-treatable diseases. In many aspects discussed above, the sulfate is even superior to the hydrochloride.

The pioglitazone salt, whether isolated or not, may have a purity of at least 70%, such as at least 90%, at least 95%, or at least 99%, wherein the percentages are based on weight. If intended for use in a pharmaceutical dosage composition, the pioglitazone salt typically has a purity of at least 99.8%, such as 99.9%.

In pharmaceutical applications, pioglitazone salts, e.g., pioglitazone sulfate, may be formulated into various solid, semisolid, or liquid compositions.

The compositions comprise pioglitazone salt and at least one pharmaceutically acceptable excipient. Pharmaceutically acceptable excipients are known in the art and include carriers, diluents, fillers, binders, lubricants, disintegrants, glidants, colorants, pigments, taste masking agents, sweeteners, plasticizers, and any acceptable auxiliary substances such as absorption enhancers, penetration enhancers, surfactants, co-surfactants, and specialized oils. The proper excipient(s) are selected based in part on the dosage form, the intended mode of administration, the intended release rate, and manufacturing reliability. Examples of common types of excipients include various polymers, waxes, calcium phosphates, sugars, etc. Polymers include cellulose and cellulose derivatives such as HPMC, hydroxypropyl cellulose, hydroxyethyl cellulose, microcrystalline cellulose, carboxymethylcellulose, sodium carboxymethylcellulose, calcium carboxymethylcellulose, and ethylcellulose; polyvinylpyrrolidones; polyethylenoxides; polyalkylene glycols such as polyethylene glycol and polypropylene glycol; and polyacrylic acids including their copolymers and crosslinked polymers thereof, e.g., Carbopol® (B. F. Goodrich), Eudragit® (Rohm), polycarbophil, and chitosan polymers. Waxes include white beeswax, microcrystalline wax, carnauba wax, hydrogenated castor oil, glyceryl behenate, glycerylpalmito stearate, and saturated polyglycolyzed glycerate. Calcium phosphates include dibasic calcium phosphate, anhydrous dibasic calcium phosphate, and tribasic calcium phosphate. Sugars include simple sugars, such as lactose, maltose, mannitol, fructose, sorbitol, saccharose, xylitol, isomaltose, and glucose, as well as complex sugars (polysaccharides), such as maltodextrin, amylodextrin, starches, and modified starches.

Solid compositions for oral administration of pioglitazone salts may exhibit immediate or extended release of the active substance from the composition. Solid pharmaceutical compositions may be formulated into tablets. The tablets may be disintegrable or monolithic. The tablets may be produced by any tabletting technique, e.g., by wet granulation, dry granulation, or direct compression.

In one embodiment, the pioglitazone salt may be formulated into rapidly disintegrable tablets, i.e., into tablets that disintegrate directly in the oral cavity, without need of swallowing them. Any conventional system/formulation for rapid disintegration can be used. Preferred however is an orally disintegrating tablet comprising at least 50% silicified microcrystalline cellulose as described in commonly-owned U.S. Provisional patent application 60/463,027, filed Apr. 16, 2003, the entire contents of which are incorporated herein by reference. The silicified microcrystalline cellulose is preferably the intimate physical mixture of colloidal silicon dioxide with microcrystalline cellulose as described in U.S. Pat. No. 5,585,115. The amount of silicon dioxide is normally within the range of 0.1 to 20 wt % and more typically 1.25 to 5 wt % such as about 2 wt %. The amount of silicified microcrystalline cellulose is preferably 50% to 90%, more preferably 60% to 80% based on the weight of the tablet.

Pioglitazone salts may also be blended into compositions that are suitable for being formulated into pellets. A plurality of pellets comprising a single dose of pioglitazone may be encapsulated into capsules made from pharmaceutically acceptable material, such as hard gelatin. In another mode, a plurality of pellets may be compressed together with suitable binders and disintegrants to form a disintegrable tablet that, upon ingestion, decomposes and releases the pellets. In yet another mode, the plurality of pellets may be filled into a sachet.

Liquid compositions, particularly aqueous compositions, may include a solution stabilizer as indicated above. The stabilizer preferably comprises a water-soluble polymer, such as hydroxypropylmethylcellulose. The concentration of the polymer in the solution can be within any of the above-described ranges but most preferably is within the range from 0.1 to 10% (w/V) of the total volume. An aqueous solution of pioglitazone sulfate typically has a pH of about 4, which is well suited for both parenteral and peroral compositions.

The liquid compositions may be parenteral compositions, but they are generally oral compositions (due to the practical medicinal use). These solutions may be aqueous, meaning that water comprises a portion of the solvent medium. Usually water comprises at least 50% of the liquid carrier, such as at least 60%, at least 80%, at least 90%, or essentially 100% of the liquid carrier. The remainder of the liquid carrier may be, for instance, ethanol. The solutions may be made by dissolving solid pioglitazone salt, e.g., pioglitazone sulfate, in an aqueous solution comprising the stabilizer, and they may also comprise suitable inert ingredient(s) such as buffers, flavors, sweeteners, etc. If necessary, the pH of the solution may be adjusted by titrating with a suitable acid or base to a desired value.

The liquid composition may also be formed by dissolving pioglitazone base with a molar equivalent of sulfuric acid (an "in situ" process). Stabilizer may be added before or after the solution is formed. Optionally, the pH is adjusted to a desired value (such as 3–5).

The liquid composition can be made initially as a concentrated solution, or suspension, and then diluted to a solution or suspension in the finished dosage form strength. Alternatively, the solution or suspension can be formed by reconstituting a dry powder of pioglitazone sulfate, with or without a stabilizer, and optionally other excipients such as pH adjuster, salts, etc. Because the reconstituted solution may be consumed relatively quickly, the solution stabilizer may not be necessary.

Pharmaceutical compositions comprising any of the water-soluble pioglitazone salts, e.g., pioglitazone sulfate, and intended as final dosage forms for administration generally contain a unit dose of pioglitazone, i.e., a therapeutically effective amount of pioglitazone for a single dose administration. The amount of the pioglitazone salt, expressed in terms of pioglitazone base, in the unit dose may contain from 1 to 100 mg, 2 to 50 mg, or 15 to 45 mg of the compound, such as an amount of 2.5, 5, 10, 15, 20, 30, or 45 mg of pioglitazone. Such a composition is normally taken from 1 to 3 times daily, such as once a day. In practice, the physician will determine the actual dosage and administration regimen, which will be the most suitable for the individual patient.

The unit dose in a tablet form can be one or more tablets administered at the same time. In the last case, several smaller tablets may be filled into a gelatin capsule to form a unit dose. The unit dose of a granulate or pellets in a capsule form may comprise a single capsule. Oral solution may be delivered in a vial or a multidose package, wherein the unit dose may be defined by the number of droplets, teaspoons, or by means of a calibrated vial.

The concentration of pioglitazone in oral or parenteral solutions is not particularly limited. For instance, it may range from 1 to 10 mg/ml, such as about 3 mg/ml.

The pioglitazone salt, e.g., pioglitazone sulfate, can be used to treat diabetes, especially type II diabetes and similar disorders caused by deficiencies in levels of blood sugar. Such disorders, treatable by pioglitazone, are known in the art. The present invention also includes the use of pioglitazone salts in the manufacture of a medicament for treating and/or preventing any one or more of these disorders. Pioglitazone compositions may be used in medical applications, e.g., in a treatment of certain forms of diabetes, either alone or in combination with other antidiabetic agents, for instance with metformin. The combination may be in the form of a single combination preparation, or by separate administration of drugs containing the above agents.

The method of treatment may comprise administering an anti-diabetic effective amount of a pioglitazone salt, e.g., pioglitazone sulfate, to a mammalian patient in need thereof. The effective amount is generally within the range of 0.1 to 1.0 mg/kg of body weight, or 10–70 mg per day. The pioglitazone salt, e.g., pioglitazone sulfate, may be administered as a unit dosage form as described above.

Each of the patents mentioned above are incorporated herein by reference in their entirety. The invention will be further described with reference to the following non-limiting examples.

EXAMPLES

Example 1

Preparation of Pioglitazone Sulfate 24 g of sulfuric acid was added slowly, at room temperature, to 250 ml of methanol followed by addition of 80 g of pioglitazone base with stirring. The mixture turned into a clear solution. 250 ml of ether was slowly added followed by 500 ml of heptane. A solid precipitated, and the suspension was stirred for 3 hours. The solid (98.4 g, yield was 96.5%) was collected by filtering and washed once with ether. The solid had a mp: 1113.5~116.5° C. (recrystallized from methanol).

Example 2

Dissolution Experiment Comparing Pioglitazone Salts

At room temperature, each pioglitazone salt (0.25 mmol) was added into 10 ml $H_2O$ with stirring.

Exp.1 (tosylate) and Exp.2 (2-napsylate) yielded unclear solutions within 1 minute. Then they quickly turned into a suspension.

Exp.3 (ethane disulfonate) and Exp.4 (sulfate) yielded clear solutions. Then they slowly turned into a suspension.

| exp. No. | Pioglitazone salt | FW | Amount | Mmol | Dissolution* |
|---|---|---|---|---|---|
| exp. 1 | tosylate | 528 | 132 mg | 0.25 | yes/no** |
| exp. 2 | 2-napsylate | 564 | 141 mg | 0.25 | yes/no** |
| exp. 3 | ethane-disulfonate | 451 | 113 mg | 0.25 | Yes |
| exp. 4 | sulfate | 454 | 114 mg | 0.25 | Yes |

*instant dissolution rate (all the salts eventually turned into pioglitazone base)
**salt was dissloved partially to form an unclear solution

Example 3

Preparation of a Stabilized Solution

The following system was tested using HPMC as an additive. Pioglitazone sulfate (100 mg) was easily dissolved in an HPMC water solution (2%, 25 ml) to form a clear solution. The solution (concentration of pioglitazone sulfate 0.4% w/v) was stable at room temperature for at least four weeks without any obvious precipitation of a solid.

Example 4

Preparation of a Drinkable Solution

To a clear solution containing 1.0 g of hydroxypropylmethylcellulose (HPMC) in 25 ml of $H_2O$ was added 125 mg of pioglitazone sulfate with stirring. A clear solution was formed that was stirred at room temperature for more than one month. No obvious solid appeared.

In view of the above description of the invention, it will be readily apparent to the worker skilled in the art that the same may be varied in many ways without departing from the spirit of the invention and all such modifications are included within the scope of the present invention as set forth in the following claims.

What is claimed is:

1. A pioglitazone sulfate.
2. The pioglitazone sulfate according to claim 1, in a solid state.
3. The pioglitazone sulfate according to claim 2, in a crystalline state.
4. The pioglitazone sulfate according to claim 1, having a molar ratio of pioglitazone moiety to sulfuric acid moiety of about 1:1.
5. A pharmaceutical composition, comprising a pioglitazone sulfate and at least one pharmaceutically acceptable excipient.
6. The composition according to claim 5, wherein said pharmaceutically acceptable excipient is a liquid carrier.
7. The composition according to claim 6, wherein said pioglitazone sulfate is dissolved in said liquid carrier.
8. The composition according to claim 7, wherein said liquid carrier is comprised of at least 50% water.
9. The composition according to claim 7, wherein said composition is an aqueous solution of pioglitazone sulfate.
10. The composition according to claim 9, which further comprises a solution stabilizer.
11. The composition according to claim 10, wherein said solution stabilizer is a polymer.
12. The composition according to claim 11, wherein said polymer is dissolved in said solution.
13. The composition according to claim 11, wherein said polymer is selected from the group consisting of hydroxypropylmethylcellulose, polyvinylpyrrolidone, and cyclodextrins.
14. The composition according to claim 13, wherein said polymer is hydroxypropylmethylcellulose.
15. The composition according to claim 10, wherein said solution stabilizer is a crown-ether.
16. The composition according to claim 10, wherein said solution stabilizer is contained in a concentration within the range from 1 to 500 mg/ml of said composition.
17. The composition according to claim 5, wherein said pioglitazone sulfate is contained in a concentration within the range front 1 to 10 mg/ml of said composition.
18. The composition according to claim 5, wherein said pharmaceutically acceptable excipient is a solid binder, carrier, or diluent.
19. The composition according to claim 18, wherein said composition is a solid oral dosage form.
20. A process of treating diabetes, which comprises:
    administering an effective amount of said pharmaceutical composition of claim 5 to a patient in need of such treatment.

* * * * *